United States Patent [19]

Arndt et al.

[11] Patent Number: 5,675,259
[45] Date of Patent: Oct. 7, 1997

[54] METHOD AND APPARATUS FOR MEASURING FLUID FLOW

[75] Inventors: G. Dickey Arndt, Friendswood; Thanh X. Nguyen; James R. Carl, both of Houston, all of Tex.

[73] Assignee: The United States of America as represented by the Administrator of the National Aeronautics and Space Administration, Washington, D.C.

[21] Appl. No.: 528,069

[22] Filed: Sep. 14, 1995

[51] Int. Cl.⁶ ................................................... G01R 27/26
[52] U.S. Cl. .................................... 324/642; 324/643
[58] Field of Search ................................ 324/637, 638, 324/642, 643, 76.56, 76.77, 76.78, 84, 92; 73/861.04; 340/603, 620

[56] References Cited

U.S. PATENT DOCUMENTS

| | | | |
|---|---|---|---|
| H395 | 12/1987 | Nash | 324/642 |
| 3,807,231 | 4/1974 | Spaw | 73/290 R |
| 3,935,970 | 2/1976 | Spaw | 222/56 |
| 4,006,407 | 2/1977 | Flaherty et al. | 324/233 |
| 4,169,543 | 10/1979 | Hail | 222/56 |
| 4,219,770 | 8/1980 | Weinert | 324/647 |
| 4,222,267 | 9/1980 | Aldrich | 73/304 C |
| 4,226,118 | 10/1980 | Aldrich | 73/290 V |
| 4,402,230 | 9/1983 | Raptis | 73/861.04 |
| 4,459,858 | 7/1984 | Marsh | 73/861.12 |
| 4,503,383 | 3/1985 | Agar et al. | 324/61 P |
| 4,554,828 | 11/1985 | Doll | 73/202 |
| 4,589,281 | 5/1986 | Aldrich | 73/290 R |
| 4,659,218 | 4/1987 | de Lasa et al. | 356/133 |
| 4,947,128 | 8/1990 | Hatton et al. | 324/640 |
| 4,947,129 | 8/1990 | Helms et al. | 324/640 |
| 4,977,915 | 12/1990 | Marrelli | 137/4 |
| 5,048,335 | 9/1991 | Marsh et al. | 73/304 C |
| 5,059,914 | 10/1991 | Lacombe et al. | 324/642 |
| 5,099,697 | 3/1992 | Agar | 73/861.04 |
| 5,101,163 | 3/1992 | Agar | 324/639 |
| 5,101,367 | 3/1992 | Agar | 364/551.01 |
| 5,140,270 | 8/1992 | Martin et al. | 324/552 |
| 5,227,730 | 7/1993 | King et al. | 324/642 X |
| 5,233,306 | 8/1993 | Misra | 324/642 X |
| 5,263,363 | 11/1993 | Agar | 73/61.44 |

OTHER PUBLICATIONS

"Electromagnetic Probe Technique for Fluid Flow Measurements", G. D. Arndt & J. R. Carl, admitted prior art.

Primary Examiner—Michael Brock
Attorney, Agent, or Firm—Hardie R. Barr

[57] ABSTRACT

Method and apparatus for making measurements on fluids related to their complex permeability are disclosed. A microwave probe is provided for exposure to the fluids. The probe can be non-intrusive or can also be positioned at the location where measurements are to be made. The impedance of the probe is determined, in part, by the complex dielectric constant of the fluids at the probe. A radio frequency signal is transmitted to the probe and the reflected signal is phase and amplitude detected at a rapid rate for the purpose of identifying the fluids. Multiple probes may be selectively positioned to monitor the behavior of the fluids including their flow rate. Fluids may be identified as between two or more different fluids as well as multiple phases of the same fluid based on differences between their complex permittivities.

45 Claims, 5 Drawing Sheets

METHOD AND APPARATUS FOR MEASURING FLUID FLOW

ORIGIN OF THE INVENTION

The invention described herein was made in the performance of work under a NASA contract and is subject to the provisions of Section 305 of the National Aeronautics and Space Act of 1958, Public Law 85-568 (72 Stat. 435; 42 U.S.C. 2457).

BACKGROUND OF THE INVENTION

1. Field of the Invention

The present invention pertains to methods and apparatus for monitoring the presence, concentration, and the movement of fluids. More particularly, the present invention relates to instrumentation and techniques for utilizing electromagnetic measurements of the complex permittivity for detecting and monitoring the behavior of fluids including measuring instantaneous changes in the flow conditions of multiple fluids or two or more states of a single fluid in a flowline or a holding container.

2. Description of Prior Art

Determining the complex permittivity of a sample under static test conditions generally requires sophisticated equipment. Equipment designed to permit such a determination is commercially available from instrumentation companies such as Hewlett Packard. However, such instrumentation used in determining the complex permittivity of samples under test is primarily suited to the measurement of solid materials, although it can be used, with more difficulty, to measure liquid samples. Various patents are provided that relate to making measurements on liquids.

U.S. Pat. No. 5,101,163 to J. Agar discloses a device for measuring the concentration of two substances through the transmission of electromagnetic waves. The device utilizes at least one transmission element for transmitting a signal and at least two receiving elements for receiving signals from the at least one transmission element for measurement purposes. Thus, a multi-antenna system is required for operation. In some cases, the transmitted signal may be relatively more difficult to receive at the receiver antennas due to the various conditions and fluids under investigation through which the transmitted signal must pass. Instrumentation or methods for determining complex permittivities are not disclosed. The device utilizes vector ratios, curve selector linearizers, and phase differences to obtain flow concentrations and velocities.

U.S. Pat. No. 5,099,697 to J. Agar discloses a device for measuring multi-phase fluid flow having a flow restrictor, first and second flow meters, and first and second pressure measurement means. No disclosure of electromagnetic wave measurements is made.

U.S. Pat. Nos. 5,101,367 and 5,263,363 to J. Agar discloses a method and apparatus for measuring the percentages of oil and water present in an oil/water mixture that requires measurement of energy absorption properties as well as flow data from a flow meter to determine which of various data curves to select so as to obtain an appropriate oil/water mixture reading. The preferred flow meter is a positive displacement flow meter and therefore necessarily mechanical in operation. The probe and related system is not particularly suitable to providing multiple measurements at different locations on the fluid without substantial increases in complexity.

U.S. Pat. No. 4,503,383 to Agar et al. discloses a device for detecting an interface between two fluids of differing electrical properties using a probe that requires an air core therein.

A paper entitled "Electromagnetic Probe Technique For Fluid Flow Measurements" by J. R. Carl and G. D. Arndt, who are listed as inventors of the present invention, describes an exemplary system that utilizes microwave techniques for measurements made on fluids. However, no disclosure is made for a means for readily distinguishing fluids having only a small difference in the real part of their complex permittivity. As well, no disclosure is made for distinguishing fluids based on their complex permittivities. Conductive fluids, such as salt water, are more accurately analyzed using both the real and imaginary parts of their permittivity. No disclosure is made of techniques for varying the field of investigation of the probe or construction techniques for this purpose. As well, no disclosure is made of techniques to increase sensitivity of the measurements by varying the phase of the reference signal. Furthermore, the paper does not disclose various modifications of the system that can be made to provide low cost sensors such as, for example only, oil/water detectors for use as reliable and simple feedback elements in an oil/water separator system.

A microwave watercut monitor is disclosed in related patents including U.S. Pat. No. 4,947,128 to Hatton et al., U.S. Pat. No. 4,947,129 to Helms et al., and U.S. Pat. No. 4,977,915 to Marrelli. The co-variance microwave watercut monitor requires a test cell suitably constructed to include antenna wave guides and a flow path adapted to receive the flowway of a petroleum stream. A microwave source provides microwave energy to a circulator which in turn provides the microwave energy to an antenna. A detector assembly connected to the circulator detects the intensity of the test microwave energy. The watercut is indicated in accordance with the intensity signal and the phase difference between the source provided microwave energy and the test microwave energy.

A monitoring system and method for detecting the presence or absence of a material at a location by utilizing an antenna and a control unit is disclosed in related patents including U.S. Pat. Nos. 4,589,281, 4,226,118, 4,169,543; and U.S. Pat. No. 4,222,267 to J. L. Adrich. The antenna provides a signal if material affecting the impedance of the antenna is in the sensing area.

U.S. Pat. Nos. 3,807,231 and 3,935,970 to R. L. Spaw disclose automatic level control systems using a single length of insulated, stranded steel cable as a radiating antenna whose reactance varies as a function of the level of material in the container adjacent the antenna.

Several patents are concerned with determining fluid flow rates. U.S. Pat. No. 4,402,230 to A. C. Raptis is directed to measurement of flow velocities of individual phases of multi-phase flow, using two probes located at different positions separated along the flow. Matched filter techniques are employed to identify the spectral signals of the individual phases, and the output signals are cross-correlated to determine the transit delay for each phase between the probes, which may be either optical, thermal or acoustical types. U.S. Pat. No. 4,459,858 to L. B. Marsh discloses an intrusive probe for use in measuring the velocity of a flowing fluid. The probe includes an electromagnet for generating an electromagnetic field in the moving fluid, and a plurality of electrodes for producing electrical signals in response to the flow of fluid through the electromagnetic field.

U.S. Pat. No. 4,554,828 to F. Doll discloses another intrusive probe including a coil for generating a magnetic field through which flows the fluid whose flow rate is to be measured. Electrodes provide a mechanism for obtaining a voltage that is proportional to the fluid flow rate. The probe is immersed in the moving fluid, and flowing fluid passes through a channel through the probe.

U.S. Pat. No. 4,659,218 to de Lasa et al. discloses fiber optic probes for sensing light intensity in monitoring characteristics of bubbles in two and three phase systems.

A level detector is disclosed in U.S. Pat. No. 5,048,335 to Marsh et al. A resonant circuit includes a capacitance probe disposed in a vessel so as to be responsive to variations in capacitance as a function of the level of material in the vessel. An oscillator is coupled to the resonant circuit and to a phase detector for detecting variations in phase angle as a function of the capacitance of the probe. The output of the phase detector is used to obtain an indication of the level of material.

U.S. Pat. No. 5,140,270 to Martin et al. discloses an apparatus for determining the quality of the dielectric material in a transformer bushing. The device uses the bushing as a capacitive element to determine the interior condition of the bushing.

Consequently, there remains a need for less complex instrumentation and techniques that provide the advantages of analysis of fluids based on their complex permittivities and techniques related thereto. It is also highly desirable to reduce the complexity of antenna arrays and offer more dependable antenna operation without the need for difficult and highly specialized mounting arrangements. Furthermore, it is desirable to provide a simplified system capable of providing the advantages of multiple simultaneous measurements at numerous locations in a container without the disadvantages of greatly increasing the amount of instrumentation for receiving, storing, and interpreting the signals from a multiple antenna system. As well, it is desirable to have a simplified construction for a multiple antenna probe assembly. It is also desirable to provide techniques for highly sensitive measurements. Those skilled in the art have long sought and will appreciate that the present invention provides solutions to these and other problems.

SUMMARY OF THE INVENTION

The present invention provides method and apparatus for making measurements on fluid relating to the complex permittivity thereof.

The probe comprises first and second electrical conductors separated by an insulator. A radio frequency signal is communicated to the probe and is, at least in part, reflected back from the portion of the probe exposed to the fluid. The radio frequency signal also provides a reference signal. An oscillator generates a second signal which is combined with each of the reference signal and the reflected signal to produce signals of a lower frequency to facilitate filtering and amplifying those signals. The two signals are then mixed in a detector to produce an output signal that is representative of the phase and amplitude change caused by the reflection of the signal at the probe as exposed to the fluid. The detector may be a dual phase detector that provides two such output signals that are in phase quadrature. A phase shifter may be provided for selectively changing the phase of the reference signal to improve the sensitivity of at least one of the output signals for more accurate readings and/or for calibration purposes. The two outputs that are in quadrature with respect to each other may be simultaneously monitored to account for drift errors. The output signals are digitized and provided to a computer at a sample rate which may be very high. The computer is operable to determine the identify the fluid based on its complex permittivity as may be useful for identifying the flow rates, determining the fluid mixture ratio, detecting impurities in the fluid, and so forth.

The probe may be co-axial in construction, with the first conductor in the form of a rod and the second conductor comprising a generally cylindrical body circumscribing the first conductor, and the annular space between the two conductors occupied by electrically insulating material. The ends of the conductors and the insulator are exposed to the fluid, either non-intrusively, or by at least partial immersion in the fluid.

In one embodiment, the probe can be very simply constructed using a common co-axial connector. By simply forming a suitable aperture in the container of the fluid to be tested, the probe can be quickly and easily adapted to virtually any container or flowline for operation. The field of investigation or desired volume of the sample to be tested by the probe can be selected within a fairly wide range and the relative spacing of the inner to outer conductor adjusted for the desired sample volume.

The simplified probe of the present invention is especially suited for use in multiple probe measurements as may be desired for many applications. Since the probe utilizes a reflected signal, only one antenna is necessary to obtain a signal. The arrangement of multiple antennas to receive multiple signals is greatly simplified because the use of the reflected signal requires only one antenna needed per signal to be received. As well, the simple antenna arrangement lends itself to the convenience and low cost of multiplexing signals from many antennas using one set of receiving equipment. The received signal may be digitized for storage at high sampling rates to thereby eliminate the need for multiple sets of receiving instruments when multiple measurements are made.

The present invention thus provides an electromagnetic measuring technique for identifying fluids by their complex permittivities and for monitoring their behavior. The present invention may be used to perform sophisticated measurements to distinguish between fluids having small differences in the real part of their complex permittivity. As well, the present invention lends itself to providing simple, low cost, go no-go detectors to distinguish between two fluids.

It would be advantageous and desirable to provide a reliable and accurate technique for detecting the presence of fluid in a combination of multiple fluids, or of detecting the presence of different states of the same fluid, or a combination of such procedures, and for monitoring the behavior of a fluid or such combinations of fluid or states of the same fluid, and it is an object of the present invention to do so. It is a further object of the present invention to provide a technique that is capable of measuring dynamically changing conditions of the material under test, and in fact to be able to measure rapidly changing conditions.

It is another object of the present invention to provide a technique whereby measurements may be made at a plurality of locations relative to fluid under test, either simultaneously or sequentially.

It is also an object of the present invention to be able to obtain measurements of fluid in a vessel, for example, either non-intrusively or at some location or locations within the interior of the fluid.

It is another object of the present invention to provide a mechanism for distinguishing between materials having small differences in the real part of their complex permittivity or relative dielectric constant.

It is yet another object to provide a simplified antenna system that is readily and quickly adaptable for taking measurements in a wide variety of fluid containers and flow tubes without any significant modification of such fluid containers or flow tubes.

These and other objects, features, and advantages of the present invention will become apparent from the drawings, the descriptions given herein, and the appended claims.

DESCRIPTION OF PREFERRED EMBODIMENTS

The present invention detects the presence of a material at a given location by sensing the complex permittivity of the material by way of the load impedance at the location. The load impedance seen by the probe at the location is determined by the complex permittivity of the material present at the location, and affects the reflection energy from the probe. As long as multiple fluids in a vessel, for example, can be identified by their complex permittivities, the present invention can distinguish such fluids. As used herein, the word "fluid" refers to liquids, vapors and gases.

Figure 1:
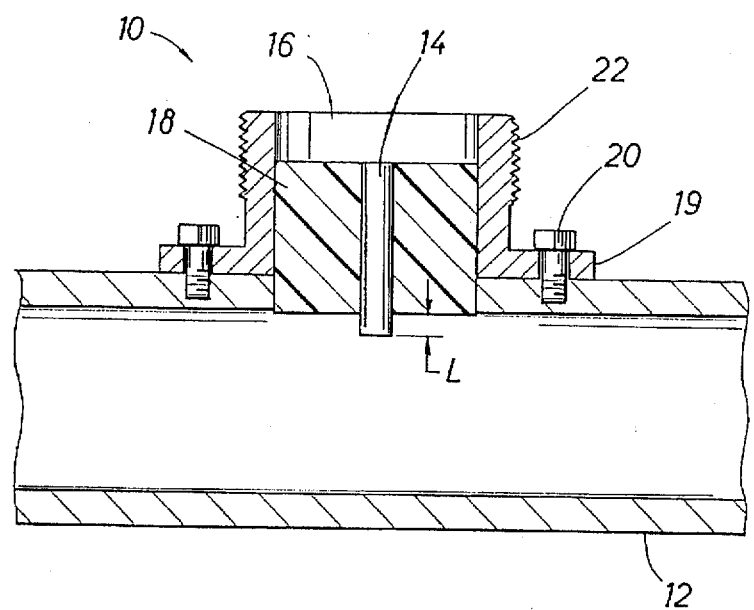
FIG. 1 is a fragmentary side elevation in partial section of an electromagnetic probe according to the present invention, as mounted on the wall of a vessel such as a pipe or tank, for example.

An electromagnetic probe according to the present invention is shown generally at 10 in FIG. 1, mounted on the wall of a vessel 12, which may be a pipe segment, a tank, or other container of fluids, for example. The probe 10 is coaxial in construction, having a first, central electrical conductor 14 in the form of a rod, generally circumscribed by a second, outer electrical conductor 16 comprising a cylindrical body, and an electrically insulating material 18, which may also include an appropriate seal, filling the annular space between the two conductors. The insulator 18 may be substantially composed of the material sold under the registered trademark "Teflon", for example. The body of the outer conductor 16 extends radially outwardly in a flange 19 by which the probe 10 is fastened to the wall of the vessel using two or more bolts or screws 20. The outer surface of the second conductor 16 features threads 22 by which a coaxial cable or other lead (not shown) may be connected to the probe. The inner and outer coaxial conductors of such a lead make electrical contact with the two probe conductors 14 and 16, respectively. Thus, as will be appreciated for a preferred embodiment, a simple co-axial connector may be used to provide an extremely low cost, easily mounted, reliable and rugged antenna construction.

It is only necessary to form a suitable aperture in virtually any shaped vessel 12. The interior portion of the aperture in a metallic vessel 12 effectively acts as an extension of outer conductor 16 to contact the fluid within vessel 12. The hole provided in the wall of the vessel 12 is just large enough to receive the insulator 18, which may also include a sealing element such as an O-ring if necessary, and to form the seal against the surface thereof. The insulator 18 extends beyond the outer conductor 16 so that, with the probe 10 fastened to the wall of the vessel 12, the extended end of the insulator is flush with the interior surface of the vessel wall. The wall of the vessel 12 serves as an extension of the outer electrode 16 to expose that conductor to the fluid in the vessel. As shown in FIG. 1, the inner conductor 14 extends through the hole in the vessel wall to a distance L beyond the end of the insulator 18. The distance L may be selected depending on the application.

The impedance of the probe 10 is used as the sensor. The load impedance seen by the probe is a function of the complex permittivity of the medium into which the probe is terminated, that is, the fluid or fluids present in the vessel 12 at the location of the probe. For a small value of the dimension L, such as zero for example, the probe 10 sees fluid only a short distance away from the face of the probe to thereby sample a small volume in its zone of investigation surrounding the probe. If it is necessary for the probe to see a larger volume of the fluid, the value of L may be increased so as to increase the volume of fluid around the central conductor 14 that affects the probe impedance and is therefore the zone of investigation of the probe. Thus, the zone of investigation of the probe can be substantially controlled with respect to the fluid to be measured and construction of the probe modified in accordance thereto. For some purposes, such as where large numbers of samples will be made for preferably small volume samples, it may be more desirable to have a smaller zone of investigation while for other purposes it may be desirable to have larger zones of investigation. Factors to consider in selecting the volume of the zone of investigation include anticipated flow rates, desirability of determining flow velocity, and the various properties of the fluids under measurement.

Figure 2:
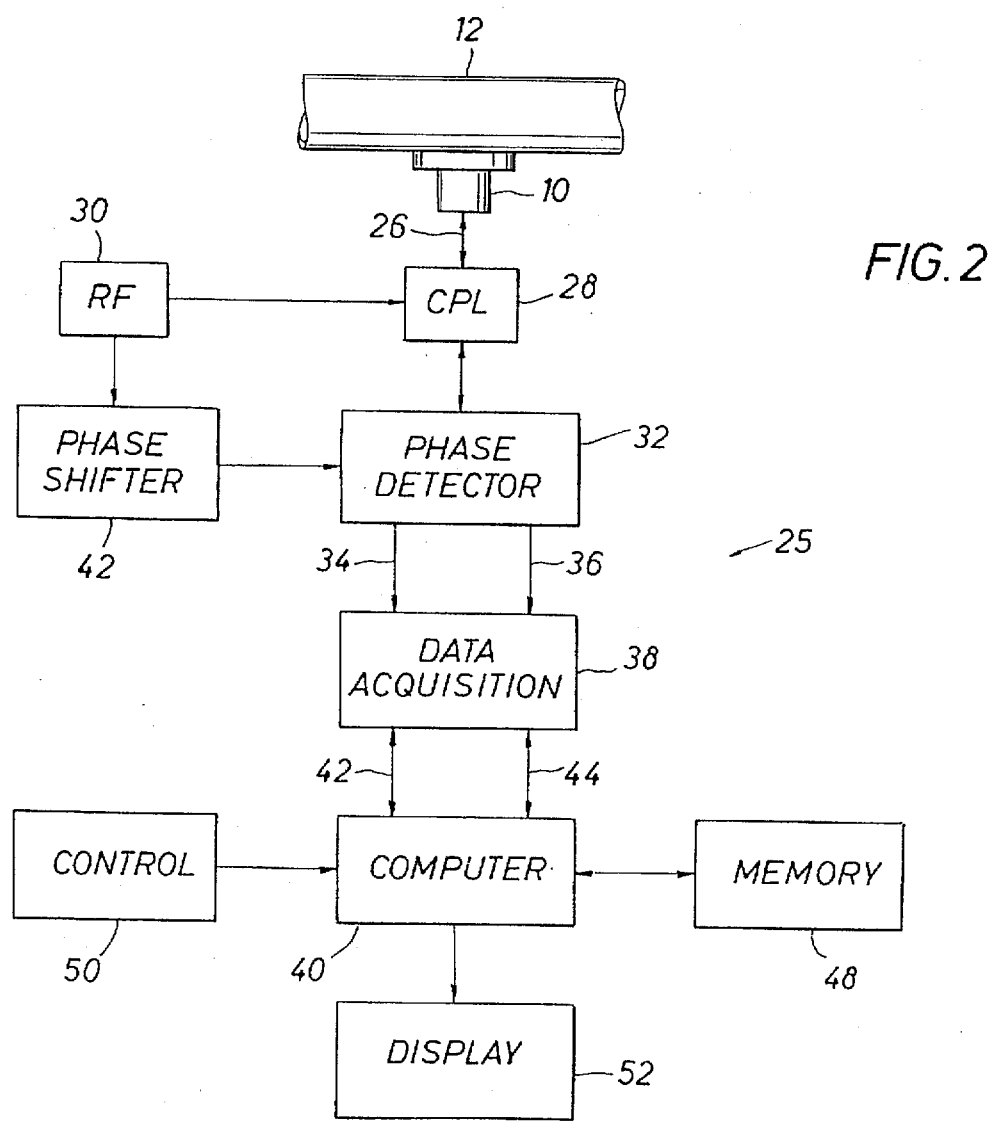
FIG. 2 is a schematic, or block diagram of an electromagnetic fluid monitoring system according to the present invention.

The phase and amplitude difference associated with a signal reflected at the interface of the probe with the fluid are quantities measured pursuant to identifying the fluid based on its complex permittivity. FIG. 2 illustrates a schematic of an electromagnetic monitoring system according to the present invention, shown generally at 25. A probe 10 mounted in the wall of a vessel 12 is connected by a low loss coaxial cable 26 to a dual phase detector 32. The probe 10 effectively continues the transmission line so that the signal reflection utilized in measuring the complex permittivity of the fluid in the container 12 occurs at the interface of the probe with the liquid where the conductors of the probe are exposed to the fluid. The RF source 30 provides a signal that is reflected at the probe/fluid interface, and the phase detector 32 measures the amplitude and phase angle change on a signal reflected from the probe 10 at approximately 1 GHz. As shown in FIG. 2, coupler 28 is connected between RF source 30, probe 10, and phase detector 32. The signal is converted to 100 MHz, amplified and the amplitude and a quadrature phase detected. Output signals 34 and 36 schematically represent the amplitude and phase information of two output signal lines which are in phase quadrature. The information is communicated to a data acquisition unit 38 wherein the signals are converted to digital form for further processing. Analysis of the signals is accomplished with an appropriate computer 40, shown communicating with the data acquisition device by way of two channels 42 and 44. It will be understood that this sequence can be provided in many different ways wherein separate lines are provided for phase and amplitude information or wherein the signals are combined. It is desirable to have the phase information be provided as a direct current output with two phases provided in quadrature with each other. A technique to obtain a more sensitive signal for the phase information involves nulling one of the outputs of the detector 32 using a phase shifter 42. This approach may provide a more sensitive measurement, and is especially useful when only one type of fluid is to be detected at the location of the probe 10 for static measurements, for example. This technique is also useful for calibration techniques before and after or at intervals during the desired measurements by which a fluid with a known complex permittivity can be measured to determine the accuracy of the system. By varying the phase of RF source 30 with phase shifter 42 the position on the sine wave at which the phase difference measurements are taken can be varied so that a more sensitive portion of the sine wave can be taken such as the zero crossing point rather than the peaks where small differences in phase may not be so readily discernable.

One advantage of having two signals in quadrature allows the two signals to be compared to check for drift errors. One method for taking advantage of this system relates to the fact that there is a constant relationship between signals in quadrature concerning the sums of their squares known to those skilled in the art that should remain constant if there are no drift errors in the system. Thus, the system as designed provides convenient means to make sophisticated measurements with minimum errors.

The computer is provided with sufficient memory 48 to store data for a measurement run obtained from an extensive number of measurements. A control unit 50 is provided in the form of a keyboard or other appropriate input device to the computer 40. A display unit 52 is provided to output the results of the data analysis. The display 52 may be a printer or video monitor, for example. The system 25 may obtain and process data at high sampling rates to effectively monitor conditions in the vessel 12 instantaneously and continuously.

As noted above, the phase, or change of phase, associated with the signal reflected at the probe 10 is the one of the quantities measured. The complex "S" factor associated with reflected energy "$S_{11}$" is given by $$S_{11} = \left( \frac{Z_0 - Z_L}{Z_0 + Z_L} \right) \tag{1}$$

where $Z_o$ is the characteristic impedance of the transmission line 26 from the phase detector 32 to the probe 10, and $Z_L$ is the probe input impedance given by R+jX with R being resistance and X being the reactance of the probe as exposed to fluid in the vessel 12. For a typical transmission cable 26, $Z_o$=50.0+j0.0 ohms. In general, $$Z_L = R + jX_c \tag{2}$$

where $$X_c = 1/(2 \pi f C_o \epsilon_r),$$

with

R=the resistance of the probe, $X_c$=the reactance of the probe, f=the frequency of the signal, Co=the air reactance of the probe, $\epsilon_r$=the relative dielectric constant of the fluid at the probe The phase angle and the magnitude of $S_{11}$ can be obtained by using Equation (2) in Equation (1) as $$\sphericalangle S_{11} = \tan^{-1} \left( \frac{100 X_C}{2500 - R^2 - X_C^2} \right) \tag{3}$$

and $$|S_{11}| = (Re[S_{11}]^2 + Im[S_{11}]^2)^{1/2}, \tag{4}$$

for a 50 ohm transmission line. For purely nonconductive fluids, the information of interest may essentially be the phase difference or angle of $S_{11}$. However, for the more general case that includes conductive fluids, such as salt water, the magnitude of $S_{11}$ is important.

The phase detector input from the probe is given by $$v_1 = v_{mag} \cos(\omega t + \theta) \tag{5}$$

where:

$V_{mag}$=the magnitude of input $v_1(t)$, and is proportional to the magnitude of $S_{11}$, $\omega$=2 $\pi$f, t=instantaneous time, and $\theta$=the phase shift of the input signal.

The angle $\theta$ is the angle of $S_{11}$ plus or minus a constant caused by the length of the transmission line between the probe and the phase detector. The reference signal input that passes through the adjustable phase shifter is given by $$v_2(t) = A \cos(\omega t + \phi) \tag{6}$$

where:

A=a constant determined by the amplitude of the reference signal, and $\phi$=the phase adjustment of the adjustable phase shifter.

The output of the phase detector may be given by $$v_0 = v_1(t) v_2(t). \tag{7}$$

If all higher frequency terms are discarded, that is, filtered out, and only the dc terms are retained, and the output of the phase detector is given by $$v_0 = \frac{V_{amp} A}{2} \cos(\phi - \theta). \tag{8}$$

In one embodiment of the present invention, Equation (8) provides an end to end system response. The angle<$S_{11}$ from Equation (3) can be substituted for $\theta$ in Equation (8), and the magnitude $|S_{11}|$ from equation (4) can be substituted for $V_{amp}$. In other embodiments, as discussed above, it may be desirable to provide the amplitude and phase difference information separately from detector circuitry 32 to data acquisition circuitry 38.

For applications where the fluid medium is relatively nonconductive, in which case there is only negligible energy coupled to the medium in the vessel 12, the probe resistance is very small, and the input impedance is essentially a capacitive reactance. Then, for a 50 ohm transmission line, Equation (3) can be written $$<S_{11} = \tan^{-1}\left(\frac{100X_C}{2500 - X_C^2}\right). \quad (9)$$

For those cases where $X_c$ is large with respect to $Z_o$ and where $<S_{11}$ is small, Equation (3) reduces approximately to $$<S_{11} \approx \frac{-100}{X_C} \text{ radians} = \frac{-5730}{X_C} \text{ degrees}. \quad (10)$$

For a certain probe with an extension L of 1 mm, the probe capacitance was measured to have been approximately 0.04 pf. Using this value and a frequency of 700 MHz, Equation (4) reduces to $$\Delta <S_{11} \approx \Delta \epsilon_r. \quad (11)$$

Thus, for a probe according to one embodiment of the present invention that provides a capacitive reactance termination for the transmission line from the phase detector, predictions can be made for the probe capacitance given the signal frequency, the probe length and the effective relative dielectric constant of the medium. Further, the sensitivity of the probe can be readily formulated.

Consider Equation (3) again. Assuming a 50 ohm transmission line, if $R^2 + X_c^2 < 2500$, then the angle of $S_{11}$ moves abruptly from negative to positive. For a low loss fluid wherein $R^2$ is negligible, setting $X_c^2 = 2500$ yields $$f = \frac{1}{100\pi C_0 \epsilon_r} \quad (12)$$

from the definition of $X_c$ above. Equation (12) provides the frequency at which the abrupt change in the angle of $S_{11}$ occurs. For example, if $C_o = 1.0$ pf and $\epsilon_r = 80$, then f=39.78 MHz. The use of this frequency could provide for an easy separation and identification of fluids having $\epsilon_r = 79$ and $\epsilon_r = 81$, for example. Thus, the present invention provides a technique whereby fluids having small differences in the real part of their complex permittivity, that is, the relative dielectric constant, can be separated by a careful choice of frequency. This approach can also be used to determine variations in a fluid from one sample to another.

While the above provides a simple but fairly sophisticated technique for identification of fluids, the same technique lends itself to a low cost go-no-go indicator for identifying fluids. Referring to FIG. 2, by simply eliminating phase shifter 42 and all elements beyond phase detector 32, the basic elements for a low cost indicator are provided. Phase detector 32 can be constructed to provide a positive or negative output depending on the type of fluid encountered. The device can be calibrated to distinguish between two liquids by simply adjusting the frequency of RF source 30. By way of example only, a low cost and compact sensor may be provided using this technique to distinguish between oil and water in an oil/water separator system. Obviously, the same technique may be used for other types of systems and for other purposes such as flow meters, level indicators, and the like as discussed hereinafter.

More generally as discussed earlier, according to the present invention, it is desirable to identify or distinguish between fluids based on their complex permittivity as a function of the phase and amplitude difference. For this purpose, the computer may be programmed to identify or distinguish fluids having different complex permittivities for each sample, preferably at a high sample rate, in response to phase and amplitude differences information as well as factors such as frequency of the radio signal and the like known to those skilled in the art. In this manner, the information can be compared to known values that may be determined by calibrating the system using the fluids involved. For instance, this technique would lend itself to determining the progress of a mixing system. By way of example only, the salinity of a salt water solution and the instantaneous changes in the solution can be determined as may be desirable in a water desalination plant or other water purification plants or as may be desirable in distilleries. As another example, it may be desirable to monitor a large scale mixing process such as for antifreeze or the like, whereby it will substantially increase the economy of the process in terms of time and energy applied thereto, to be able to determine the state of the mixture at any moment in time by having the capability to monitor the substantially instantaneous change during the mixture process. A single probe may be mounted at an appropriate position in a mixing tank, for example, to monitor the change from one fluid to another as a function of time.

For substantially immiscible fluids, the system can be calibrated by, for instance, determining a plot of amplitude difference versus phase difference for each fluid to be identified. The plot of each fluid will be different, and therefore distinguishable, based on its complex permittivity. Samples may be taken at high rates that may vary from 500 to over 100,000 samples per second depending on various factors such as velocity of fluid flow and the like. The computer can be programmed to identify the fluid of each sample. The percentages of each fluid identified by the system can then be determined. As discussed hereinafter, multiple probes can be used to assure that the samples taken are an accurate representation of the fluid flow. The present invention provides a relatively simple installation for multiple probes.

For measuring percentage mixtures, such as salinity, that may have a complex permittivity that varies gradually rather than producing a particular identifiable plot, the system can be calibrated based on several known samples. In this manner, for instance, the salinity of the fluid sampled by one or more probes may be determined for each sample at a very high sample rate by interpolation between the values for the known samples as necessary.

There are many applications for a single, non-intrusive, easily mounted probe as illustrated in FIG. 1. For example, the probe 10 mounted at the top of a vessel 12 as shown in FIG. 1 can be used to determine whether liquid is present at that level, and thus serve as a void detector. A probe 10 mounted at the bottom of a vessel can be used to continuously monitor the purity of liquid in the vessel. Also, a single probe positioned on a pipeline can be used to identify fluid flow regimes along the pipe. A single probe may be used to identify laminar flow or turbulent flow. In general, a single, non-intrusive probe may be appropriately placed on a pipe, tank or other type of vessel containing one or more fluids to monitor the fluid or fluids at the location of the probe, to detect changes in the fluid or fluids at the location of the probe as a function of time, and to detect the presence or absence of fluid at the level of the probe to identify a full or empty vessel, or whether the vessel contains liquid up to the level of the probe. As well, impurities in a product may be identified substantially instantaneously by monitoring the product using a system according to the present invention.

Multiple non-intrusive probes according to the present invention can be utilized to perform all of the operations that a single probe can be used to accomplish. Multiple probes may be mounted on a vessel to perform some tasks more conveniently than can be done with a single probe, or to perform tasks that cannot be done with a single probe. For example, identifying flow regimes, and calculating volume fractions may be accomplished more conveniently with multiple probes located at different positions on a pipeline and performing additional data processing. Flow velocity determinations require at least two probes located at a known displacement along the direction of flow.

Figure 3:
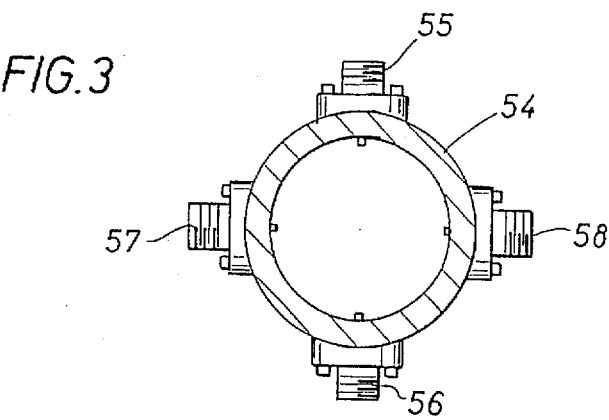
FIG. 3 is an end elevation of a section of pipe fitted with four probes located on the top, the bottom and opposite side positions of the pipe, according to the present invention.
Figure 4:
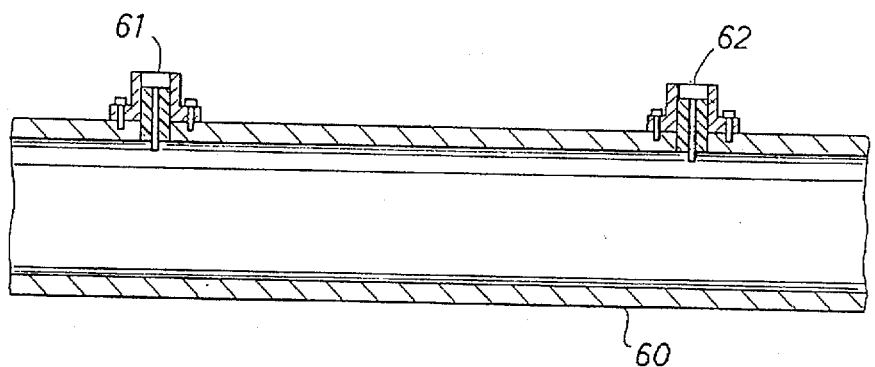
FIG. 4 is a fragmentary side elevation of a section of pipe fitted with multiple probes longitudinally displaced along the pipe according to the present invention.
Figure 5:
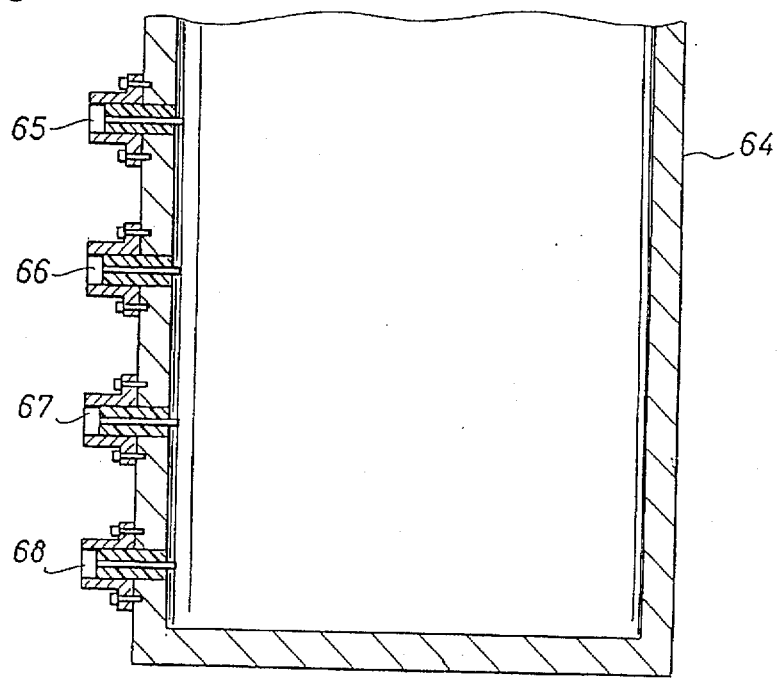
FIG. 5 is a fragmentary side elevation in partial section of a tank fitted with a plurality of probes located at different heights along the tank according to the present invention.

FIG. 3 illustrates a pipe 54 with four non-intrusive probes 55, 56, 57 and 58 mounted at four different circumferential positions around the pipe to monitor the conditions at the top, bottom and sides, respectively, of the flowline. Such an array of probes can be used to monitor two fluids in the same pipe 54, or two states of the same fluid, for example. FIG. 4 shows a pipe 60 having two non-intrusive probes 61 and 62 located at different longitudinal positions along the pipe to monitor changes in flow conditions linearly along the flowline. For example, the probes 61 and 62 may be used to detect a change of flow between turbulent and laminar. If the distance between the two probes 61 and 62 is known, flow velocity measurements may be made. This can be accomplished using any of the above techniques whereby data from probe 61 and 62 is stored to form two streams of data. Assuming the relative structure of the fluid does not change significantly between the time the fluid flows from probe 61 to probe 62, there will be a match in the data streams with a corresponding time interval lag therebetween. The time interval can be compared with the distance between the probes to determine the flow velocity. Due to the very high sampling rates available, the probes may be quite close to each other for this purpose. The multiple probe configurations discussed hereinafter are also suitable for this purpose depending on orientation within the flowline.

Figure 6:
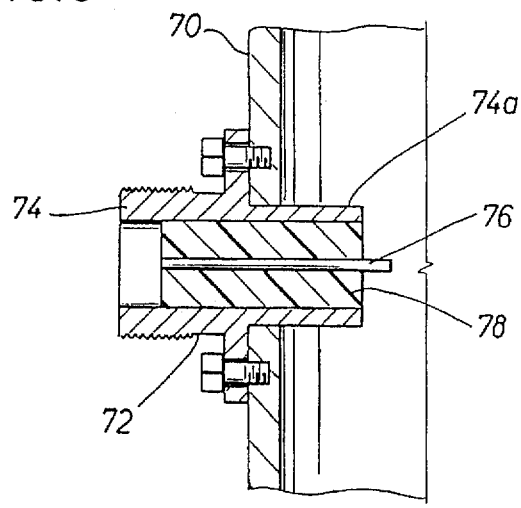
FIG. 6 is a fragmentary side elevation in cross section of a vessel fitted with a probe extending to a position within the vessel according to the present invention.

FIG. 6 shows a tank 64 with four non-intrusive probes 65, 66, 67 and 68 mounted at different heights along the side of the tank. The array of probes 65–68 can be used to determine the depth of material in the tank 64. Also, such an array can be used to monitor the rate of mixing of two liquids in the tank 64, or the rate at which a liquid, or solid material, dissolves in a solvent, for example.

Intrusive probes according to the present invention may be utilized to monitor conditions at locations in the interior of a vessel. One form of such an intrusive probe according to the present invention is illustrated in FIG. 6, mounted on the side wall of a vessel 70. The probe 72 is similar in construction to the probe 10 illustrated in FIG. 1, having an outer conductor 74 by which the probe is fastened to the vessel 70° an inner conductor 76 and an insulator 78. However, the two conductors 74 and 76, as well as the insulator 78, all extend a selected distance within the vessel 70 beyond the interior surface of the vessel wall, the outer conductor featuring an extended neck 74a. The probe 72 is thus exposed to fluid at the location within the vessel 70 and away from the side wall thereof, at the end of the interior conductor 76. Consequently, the measurements obtained with the probe 72 are of conditions at that point in the vessel interior.

The intrusive probe 72 of FIG. 6 may be very useful in monitoring conditions at a point within a vessel as described, particularly in cases wherein the fluid or fluids being monitored are not intended to flow. For monitoring conditions in moving fluid, the shape and size of the probe should be chosen to minimize unwanted resistance to the fluid flow. Further, intrusive probes should be sufficiently strong to withstand the forces generated by the flowing fluid, and resistant to corrosion and abrasion. Also, in some applications multiple interior locations are to be monitored, requiring multiple intrusive probes. For example, in the oil and gas industry there is a need to measure the volume fraction of oil, water and natural gas flowing through a pipe, as well as the velocity of each fluid. By placing probes at various strategic locations within a cross section of the pipe, the volume fractions of each constituent can be determined. Also, by using an identical probe configuration downstream from the first probe configuration, the velocity of each constituent can be measured in most cases.

Figure 7:
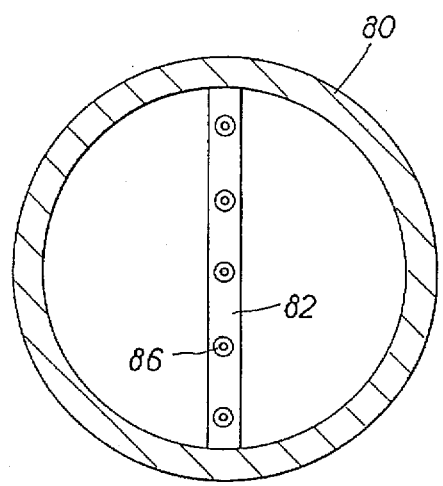
FIG. 7 is a schematic end view of a section of pipe with multiple probes positioned at locations within the interior of the pipe section according to the present invention.
Figure 8:
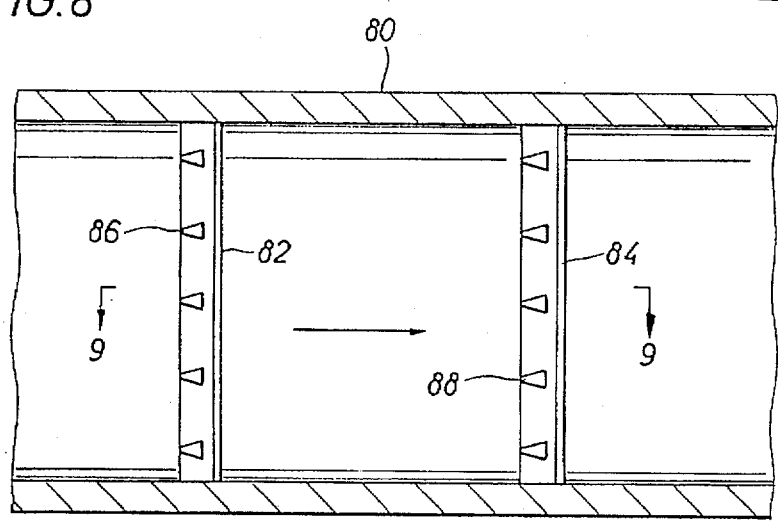
FIG. 8 is a schematic side elevation in partial section of the pipe section of FIG. 7, showing the positioning of two sets of internal probes according to the present invention.
Figure 9:
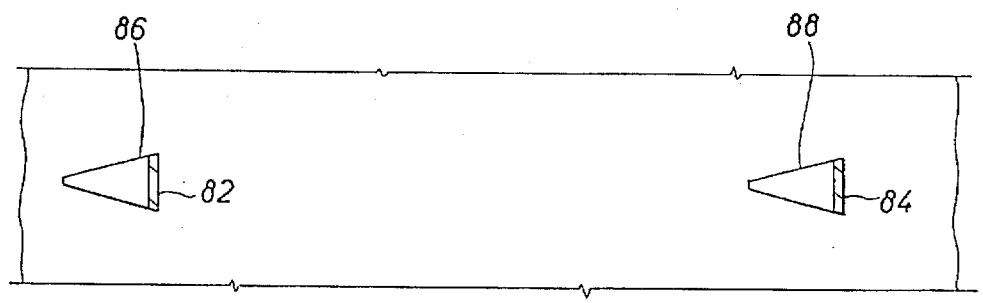
FIG. 9 is an enlarged, schematic plan view, in partial section, taken along line 9—9 in FIG. 8, showing the streamline profile of the probes.

FIGS. 7, 8 and 9 show three views of a pipe 80 fitted with two vertical columns 82 and 84, with each column supporting a set of five probes 86 and 88, respectively. Fluid flow in the pipe 80 is from left to right as viewed in FIGS. 8 and 9, and into the page as viewed in FIG. 7. The horizontal profiles of the columns 82 and 84, and of the probes 86 and 88, are generally wedge-shaped, as best seen in FIG. 9, with the apex of each wedge oriented upstream. The columns 82 and 84, and the probes 86 and 88, are thus constructed and oriented to minimize flow resistance. Although the probes 86 and 88 are shown schematically, their general construction is preferably coaxial. Each of the downstream probes 88 is located directly behind a corresponding upstream probe 86. With this array of intrusive probes, volume fractions and individual velocities of constituents of a nonhomogeneous mixture of natural gas, oil and water, for example, may be measured. With such an array of probes, or some other arrangement of multiple intrusive probes, monitoring of flow regimes,and flow profiles can be carried out, and blob statistics can also be obtained.

When multiple probes are arrayed for monitoring conditions at different locations in or along a vessel, each probe can be part of a separate detector system of the type illustrated at 25 in FIG. 2, and the data acquired and processed by each of the systems correlated to produce the desired information. Alternatively, a single phase and amplitude detector may be utilized with a multiplexor (see FIG. 11) positioned to receive the signals from all of the probes and to multiplex the signals to the detector. The output of the detector would also be multiplexed to sample-and-hold circuits assigned to specific probes as desired. As another alternative, a single circuit can be utilized with multiple channels and phase and amplitude detector circuits to accommodate the outputs from multiple probes.

Figure 10:
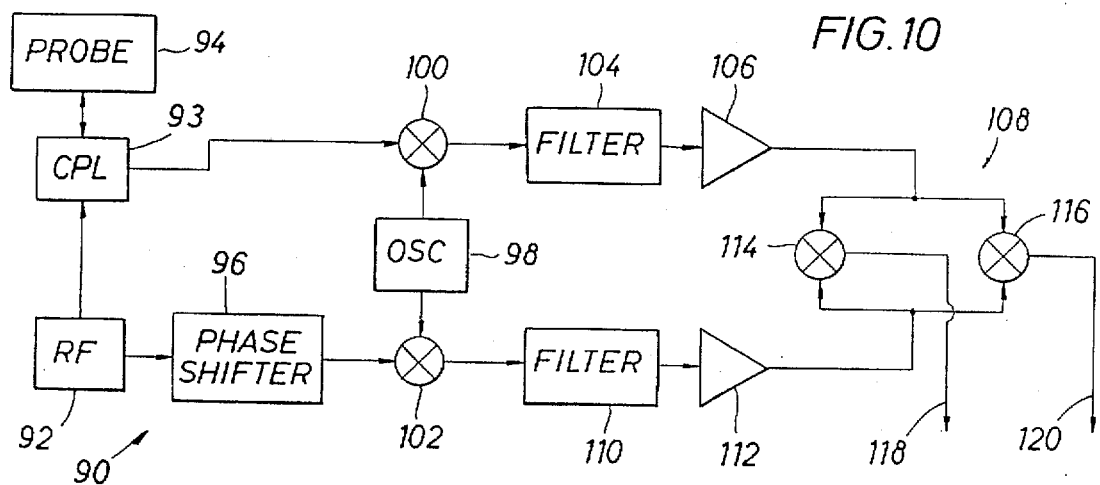
FIG. 10 is a schematic illustration of a detector for use as part of the monitoring system according to the present invention.

FIG. 10 illustrates a schematic for a phase and amplitude detector system shown generally at 90 that may be part of the system 25 of FIG. 2, for example. A radio frequency signal, say at 1 GHz, from a source 92 is reflected at the probe 94, and, in another branch of the circuit, serves as a reference signal subject to selective phase shifting at 96. A local radio frequency oscillator 98 is used to convert the reflected signal and the reference signal to lower frequency, say 100 MHz, at 100 and 102, respectively to facilitate filtering and amplification. The converted reflected signal is filtered at 104 and amplified at 106, and the converted phase and amplitude information signal is filtered at 110 and amplified at 112. The reflected signal and the reference signal are mixed in a dual phase and amplitude detector at 108, utilizing two detector circuits 114 and 116. It may be desirable to produce a difference signal output comprising a dc voltage signal that is a function of the phase difference and amplitude difference on the two 100 MHz channels. The output from the dual detector 108 may comprise at least two dc signals that are in phase quadrature. Instantaneous phase and amplitude can then be derived from either channel; by using both channels a calibration can be provided to account for drift and/or for determining the conductivity of the fluid. While the amplitude difference may be derived as a part of this system in detector 108, it may also be detected at another portion of the system as may be desired.

Figure 11:
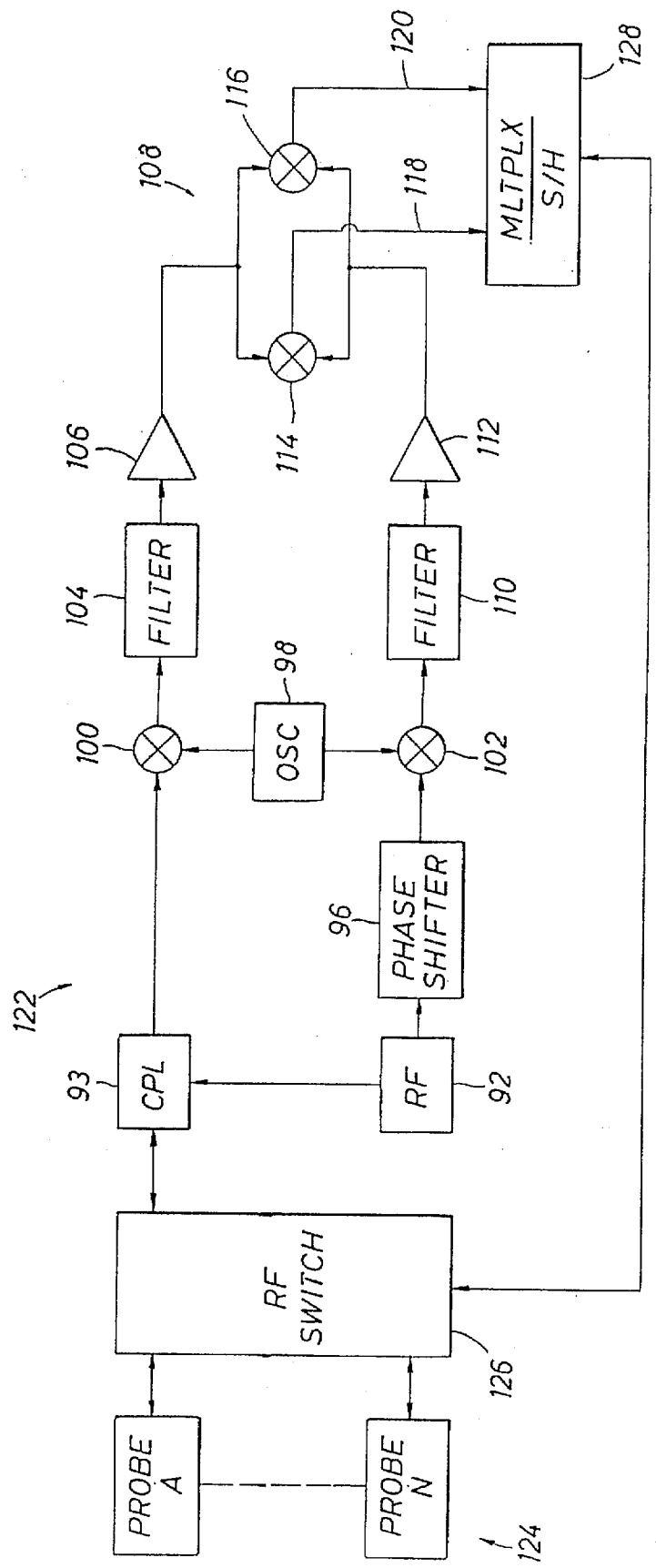
FIG. 11 is a schematic illustration of a three-channel detector for use with three probes according to the present invention.

FIG. 11 shows a schematic of a variation of the detector 90 that is illustrated in FIG. 10 in conjunction with a single probe. The detector shown generally at 122 in FIG. 11 is able to accommodate any number of the relatively simple probes of the present invention. An indeterminate number of N probes are indicated generally at 124, with each probe connected to an RF switching circuit 126, one side of which is connected to the coupler 93. The remainder of a detector circuit such as that shown at 90 in FIG. 10 is incorporated in the multiple-probe detector 122, including components 96–116. The switch 126 multiplexes the signals between the coupler 93 and each of the probes 124 so that the reflected signal from each of the N probes is individually processed by the detector circuitry 122.

Figure 12:
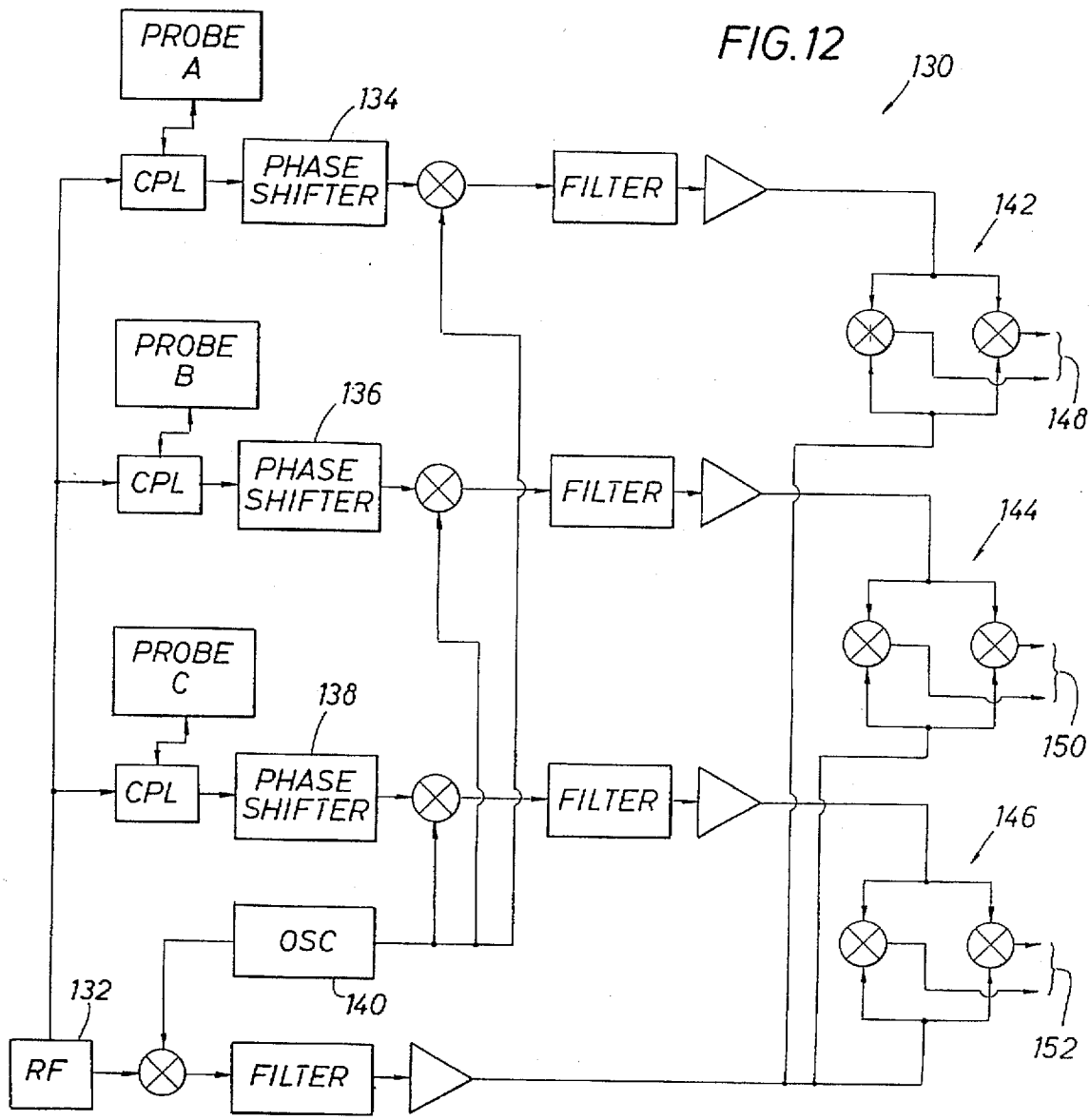
FIG. 12 illustrates a schematic for a three-channel detector.

FIG. 12 illustrates a schematic for a three-channel detector shown generally at 130 for use with three probes, and which is a variation of the single probe schematic illustrated in FIG. 10. A single source 132 provides a radio frequency signal that is reflected at three probes A, B and C, with the reflected signals separately phase-shifted at 134, 136 and 138, respectively. A single local oscillator is used to convert the reflected, phase-shifted signals to a lower frequency for filtering and amplification. The oscillator also converts a reference signal from the source 132 to the same lower frequency, for filtering and amplification. The reference signal is then mixed with each of the processed reflected signals from the probes A, B and C in three dual detectors 142, 144 and 146. Each of the three detector circuits 142, 144 and 146 may produce a pair of dc voltage signals that are in phase quadrature, 148, 150 and 152, respectively. It will be appreciated that the schematic 130 may be provided with any number of channels for use with a like number of probes.

The present invention thus provides a technique for detecting and monitoring multiple fluids, and states of fluids, utilizing the effect the fluids have on the reflection of radio frequency signals, communicated to a probe according to the present invention, at the interface between the electrodes, or conductors, of the probe and the fluid being measured. Many variations in the above system may be made including the various takeoff points for signals in the circuitry or components used in the circuitry to obtain the phase and amplitude differences used to distinguish or identify fluids based on the complex permittivity of the sample under test.

The foregoing disclosure and description of the invention is illustrative and explanatory thereof, and various changes in the method steps as well as the details of the apparatus may be made within the scope of the appended claims without departing from the spirit of the invention.

What is claimed is:

1. A method for making measurements on at least one fluid, comprising the following steps:

providing first and second electrodes in concentric relationship with each other to form a sensing probe, said first and second electrodes being electrically insulated from each other;

exposing an end portion of said sensing probe to said at least one fluid;

transmitting a radio signal to said sensing probe through a signal transmission cable;

receiving a reflected signal from said sensing probe with signal transmission cable;

phase detecting to produce a first output signal that contains phase difference and amplitude difference information with respect to said reflected signal and a reference signal;

repetitively sampling and digitizing said first output signal to produce a plurality of samples; and identifying said at least one fluid for each of said plurality of samples based on a complex permittivity of said at least one fluid.

2. The method of claim 1, further comprising:

phase detecting to produce a second output signal that is a function of a phase difference and an amplitude difference between said reflected signal and said reference signal, said second output signal being in phase quadrature with said first output signal.

3. The method of claim 2, further comprising:

controlling said first output signal and said second output signal by varying the phase of said reference signal.

4. The method of claim 3, wherein said step of controlling further comprises:

selectively nulling either said first output signal or said second output signal by varying the phase of said reference signal.

5. The method of claim 3, wherein said step of controlling further comprises:

increasing phase discrimination sensitivity of said first output signal for said phase difference between said reflected signal and said reference signal by varying the phase of said reference signal.

6. The method of claim 2, further comprising:

monitoring signal drift of said first output signal by comparing said first output signal and said second output signal.

7. The method of claim 1, further comprising:

exposing said end portion of said sensing probe to a plurality of known test fluids;

storing the amplitude difference and phase difference information with respect to each of said plurality of known test fluids to provide calibration values; and comparing said calibration values with said plurality of samples.

8. The method of claim 1, wherein said step of providing said first and second electrodes further comprises:

selecting a desired volume of said at least one fluid to be investigated by said sensing probe to form a preselected investigation zone surrounding said sensing probe containing said desired volume of said at least one fluid; and extending said first conductor a selected amount beyond said end portion of said second conductor to provide that said sensing probe investigates said desired volume of fluid in said preselected investigation zone.

9. The method of claim 8, further comprising:

providing a plurality of said sensing probes with each sensing probe having said first conductor extended a selected amount to form a corresponding preselected investigation zone surrounding each of said plurality of said sensing probes.

10. The method of claim 9, further comprising:

vertically orienting said plurality of sensing probes with respect to each other within a container; and determining a level of said at least one fluid in said container.

11. The method of claim 9, further comprising:

orienting said plurality of sensing probes in a flowline substantially along a direction of flow of said at least one fluid within said flowline; and determining a velocity of said at least one fluid within said flowline.

12. The method of claim 8, further comprising:

providing first and second fluids to be measured;

repetitively sampling said preselected investigation zone with said sensing probe to obtain said plurality of samples;

storing said sample results;

distinguishing said first fluid from said second fluid for each of said plurality of samples; and obtaining a sample percentage mixture of said first fluid with respect to said second fluid for said plurality of samples.

13. The method of claim 1, further comprising:

providing a plurality of said sensing probes with each of said plurality of sensing probes being in communication with a respective portion of said at least one fluid;

transmitting said radio signal to each of said plurality of sensing probes;

receiving a respective reflected signal from each of said plurality of sensing probes;

obtaining said plurality of samples from said plurality of sensing probes; and identifying said at least one fluid for each of said plurality of samples based on a complex permittivity of said at least one fluid.

14. The method of claim 13, wherein said step of obtaining a complex permittivity further comprises:

multiplexing said respective reflected signal from each of said plurality of sensing probes to a phase detector.

15. The method of claim 1, further comprising the step of:

providing first and second fluids for making measurements, said first fluid having a complex permittivity with a real part having a first value, said second fluid having a complex permittivity with a real part having a second value; and selecting a frequency of said radio signal corresponding to a complex permittivity having a real part with a value between said first value and said second value.

16. The method of claim 15, wherein said first value and said second value are relatively close.

17. The method of claim 1, wherein said step of providing first and second electrodes further comprises:

utilizing a co-axial cable to form said sensing probe.

18. The method of claim 1, wherein said step of providing first and second electrodes further comprises:

utilizing a co-axial cable connector to form said sensing probe.

19. The method of claim 18, further comprising:

providing a cylindrical end portion on said co-axial cable connector, and connecting said signal transmission cable to said cylindrical end portion.

20. A method for making measurements, comprising the following steps:

providing first and second fluids, said first fluid having a complex permittivity with a real part having a first value, said second fluid having a complex permittivity with a real part having a second value;

providing first and second electrodes to form a sensing probe;

exposing an end portion of said sensing probe to at least one of said first and second fluids;

providing a signal transmission cable for electrically coupling to said sensing probe;

transmitting a radio signal to said sensing probe through said signal transmission cable;

selecting a frequency of said radio signal corresponding to a complex permittivity having a real part with a value between said first value and said second value;

mixing said radio signal with a waveform received in response to said step of transmitting to thereby obtain an output signal; and monitoring said output signal to distinguish between said first and second fluids.

21. The method of claim 20, wherein said step of providing first and second fluids further comprises:

providing said first and second fluids such that there is a relatively small difference between said first and second values.

22. The method of claim 20, wherein said first fluid is oil and said second fluid is water, said method further comprising:

distinguishing oil from water.

23. The method of claim 20, wherein said step of monitoring further comprises:

monitoring the plurality of said output signal to distinguish between said first and second fluids.

24. The method of claim 20, further comprising:

changing the phase of said radio signal to obtain a phase controlled signal; and mixing said phase controlled signal with said waveform received in response to said step of transmitting.

25. The method of claim 20, further comprising:

providing a plurality of sensing probes;

obtaining a respective output signal corresponding to each of said plurality of sensing probes; and selectively monitoring the polarity of said respective output signal to distinguish between said first and second fluids.

26. The method of claim 20, further comprising:

providing a plurality of probes at various heights in a container;

monitoring a respective output from each of said plurality of probes; and determining a level of said first or second fluid in said container.

27. The method of claim 20, further comprising:

providing an upstream probe and a downstream probe in a flowline;

monitoring an upstream output and a downstream output from respective of said upstream probe and said downstream probe; and determining a rate of flow of said first and second fluids through a flowline.

28. Apparatus for making measurements on at least one fluid, comprising:

at least one sensing probe including first and second coaxially disposed electrodes having insulating means disposed therebetween, said first and second electrodes having respective end portions for exposure to said at least one fluid;

a radio frequency source for producing a radio signal;

a signal transmission line for transmitting said radio signal to said at least one sensing probe;

a signal receiver for receiving a reflection signal from said at least one sensing probe reflected in response to said at least one fluid;

phase detector circuitry for producing a first output signal that includes phase and amplitude difference information with respect to said reflection signal and said radio signal;

analog-to-digital circuitry for digitizing said first output signal to form a digitized first output signal, said analog-to-digital circuitry being operable to provide at least five hundred of said digitized first output signals per second; and circuitry operable for identifying said at least one fluid based on a complex permittivity of said at least one fluid for each of said digitized first output signals.

29. Apparatus as defined in claim 28, wherein:

said phase detector circuitry is operable for producing a second output signal in phase quadrature with said first output signal.

30. Apparatus as defined in claim 29, further comprising:

an adjustable phase shifter for receiving said radio signal and for selectively shifting the phase of said radio signal.

31. Apparatus as defined in claim 28, wherein:

said first electrode comprises a rod, said second electrode comprises a substantially cylindrical body, and said insulating means comprises insulating material that extends from said first electrode to said second electrode, said end portions of said electrodes and an end portion of said insulating material being exposed to said at least one fluid.

32. The apparatus as defined in claim 28, wherein said at least one sensing probe further comprises:

a co-axial cable connector having thereon a receptacle to receive a co-axial cable.

33. The apparatus as defined in claim 32, wherein:

said first electrode is a center conductor of a co-axial cable connector.

34. The apparatus as defined in claim 32, further comprising:

a substantially metallic vessel for said at least one fluid, said cable connector having a portion extending through an aperture in said metallic vessel, said aperture having a metallic wall forming at least a portion of said second electrode.

35. Apparatus as defined in claim 28, further comprising:

a plurality of sensing probes, each of said plurality of sensing probes receiving said radio signal and producing a respective reflection signal.

36. Apparatus as defined in claim 35, further comprising:

a multiplexor for sequentially sampling each said respective reflection signal.

37. Apparatus as defined in claim 28, further comprising:

intermediate frequency mixer to significantly lower the frequency of said radio signal and said reflection signal.

38. Apparatus as defined in claim 28, further comprising:

a plurality of sensing probes; and a multiplexor for sequentially sampling a respective signal from each of said plurality of sensing probes, said phase detector circuitry sequentially providing a plurality of output signals each being a function of a phase difference and an amplitude difference between said reflection signal and said radio signal.

39. Apparatus as defined in claim 28, wherein:

said first electrode extends a selected amount beyond said end portion of said second electrode and said end portion of said insulating material, said selected amount being functionally related to a desired volume of said at least one fluid to be sampled.

40. Apparatus for making measurements on first and second fluids having first and second real parts of their respective complex permittivities, said first and second fluids being disposed within a container, comprising:

a sensing probe having first and second electrodes and being electrically insulated with respect to each other, said container having an aperture therethrough to receive said sensing probe;

a radio signal transmitter operable to apply a radio signal to said sensing probe, said radio signal transmitter having circuitry tuned to provide said radio signal with a frequency corresponding to a real part of a complex permittivity between said first and second real parts of said respective complex permittivities;

phase detector circuitry for producing a first output signal that includes phase and amplitude difference information with respect to said reflection signal and said radio signal; and a monitor for receiving said output signal and distinguishing between said first and second fluids.

41. The apparatus of claim 40, wherein said monitor further comprises:

circuitry for distinguishing between a polarity of said output signal.

42. The apparatus of claim 40, wherein said monitor further comprises:

a computer.

43. The apparatus of claim 40, wherein said sensing probe further comprises:

a co-axial connector.

44. The apparatus of claim 40, wherein said first and second fluids comprise oil and water.

45. The apparatus of claim 40, wherein there is a relatively small difference between said first and second real parts of said respective complex permittivities.

* * * * *